(12) United States Patent
Jackson et al.

(10) Patent No.: US 7,136,837 B2
(45) Date of Patent: Nov. 14, 2006

(54) PROVIDING A DISCOUNTED PAYMENT SCHEDULE FOR UTILIZING AND DELETING STORED IMAGES

(75) Inventors: William M. Jackson, Victor, NY (US); Kenneth A. Parulski, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/842,201

(22) Filed: May 10, 2004

(65) Prior Publication Data

US 2004/0210534 A1 Oct. 21, 2004

Related U.S. Application Data

(63) Continuation of application No. 09/730,703, filed on Dec. 6, 2000, now Pat. No. 6,760,128.

(51) Int. Cl.
*G06F 17/60* (2006.01)

(52) U.S. Cl. ..................... 705/52; 358/1.15; 358/487; 707/10; 707/104.1; 707/3; 709/217; 709/203; 709/218; 705/1; 705/2; 705/26

(58) Field of Classification Search .................. 705/52, 705/1, 2, 26; 358/1.15, 487; 707/10, 104.1; 709/203, 217
See application file for complete search history.

(56) References Cited

U.S. PATENT DOCUMENTS 5,164,831 A * 11/1992 Kuchta et al. ............ 348/231.7
5,666,215 A 9/1997 Fredlund et al.
6,004,061 A 12/1999 Manico et al.
6,760,128 B1 * 7/2004 Jackson et al. .............. 358/453

FOREIGN PATENT DOCUMENTS

JP  WO 2001/24050   * 4/2001
WO  WO 00/01138      1/2000

OTHER PUBLICATIONS

FOTOSTATION 4.0. Dec. 23, 199. http://www.quiknet.com/~frcn/FotoStation.html. Retrived online Nov. 30, 2004.*
U.S. Appl. No. 09/691,364, filed Oct. 18, 2000, entitled Effective Transfer of Images from a User to a Service Provider.
U.S. Appl. No. 09/347,310, filed Jul. 2, 1999, entitled Albuming Method with Automatic Page Layout.
U.S. Appl. No. 09/199,724, filed Sep. 20, 2000, entitled CMOS Active Pixel with Scavenging Diode.
U.S. Appl. No. 09/534,469, filed Mar. 24, 2000, entitled Configuring and Purchasing Imaging Devices.
U.S. Appl. No. 09/199,639, filed Nov. 25, 1998, entitled Photocollage Generation and Modification Using Image Recognition.

(Continued)

*Primary Examiner*—James A Reagan
(74) *Attorney, Agent, or Firm*—Raymond L Owens

(57) ABSTRACT

A method of selecting images from a plurality of images previously transferred from a user and stored by a service provider, and ordering services to be provided utilizing the images, including establishing an account for the user with the service provider to permit the user to have access to ordered services; receiving a plurality of images from the user and storing the plurality of images in an electronic database provided by the service provider; displaying image designators for at least a subset of the images for viewing by the user; the user selecting a service to be provided using at least one selected image from the plurality of images stored in the electronic database, providing a price and a lower discounted price for the selected service; and using the discounted price if the user deletes at least one of the plurality of images from the electronic database.

13 Claims, 12 Drawing Sheets

OTHER PUBLICATIONS

U.S. Appl. No. 08/977,382, filed Nov. 24, 1997, entitled Electronic Camera with "Utilization" Selection Capability.

CompactFlash Specification Version 1.3 published by the CompactFlash Association, Palo Alto, California, Aug. 5, 1998.

"Digital Still Camera Image File Format (Exif)" version 2.1, Jul. 1998 by the Japan Electronics Industries Development Association (JEIDA) Tokyo, Japan.

* cited by examiner

```
 1
 2
 3    USER NAME
 4    PASSWORD
 5    USER E-MAIL ADDRESS
 6    USER SHIPPING ADDRESS
 7    BILLING INFORMATION
 8
 9    DESIGNEE #1    SHIPPING ADDRESS
10
11    DESIGNEE #2    SHIPPING ADDRESS
12
13    IMAGE LIST
14         IMAGE 1:       DCP_0012.JPG     UPLOADED 14/01/1999
15         IMAGE 2:       DCP_0013.JPG     UPLOADED 14/01/1999
16         IMAGE 3:       DCP_0017.JPG     UPLOADED 14/01/1999
17         IMAGE 4:       DCP_0018.JPG     UPLOADED 14/01/1999
18         ...
19         IMAGE 55:      DCP_0202.JPG     UPLOADED 12/03/1999
20         IMAGE 56:      DCP_0213.JPG     UPLOADED 12/03/1999
21         IMAGE 57:      DCP_0217.JPG     UPLOADED 12/03/1999
22         IMAGE 58:      DCP_0228.JPG     UPLOADED 12/03/1999
23         ...
24         IMAGE 109:     DCP_0333.JPG     UPLOADED 17/09/1999
25         IMAGE 110:     DCP_0334.JPG     UPLOADED 17/09/1999
26         IMAGE 111:     DCP_0337.JPG     UPLOADED 17/09/1999
27         IMAGE 112:     DCP_0339.JPG     UPLOADED 17/09/1999
28         ...
29         IMAGE 333:     DCP_1317.JPG     UPLOADED 02/01/2000
30         IMAGE 334:     DCP_1318.JPG     UPLOADED 02/01/2000
31         IMAGE 335:     DCP_1322.JPG     UPLOADED 02/01/2000
32         IMAGE 336:     DCP_1324.JPG     UPLOADED 02/01/2000
33         ...
34         IMAGE 512:     DCP_1781.JPG     UPLOADED 05/05/2000
35         IMAGE 513:     DCP_1783.JPG     UPLOADED 05/05/2000
36         IMAGE 514:     DCP_1787.JPG     UPLOADED 05/05/2000
37         IMAGE 515:     DCP_1788.JPG     UPLOADED 05/05/2000
38         ...
39         IMAGE 602:     DCP_2171.JPG     UPLOADED 12/05/2000
40         IMAGE 603:     DCP_2172.JPG     UPLOADED 12/05/2000
41         IMAGE 604:     DCP_2174.JPG     UPLOADED 12/05/2000
42         IMAGE 605:     DCP_2179.JPG     UPLOADED 12/05/2000
43
44
```

FIG. 5A

```
45    PRODUCT ID -1
46    PRODUCT TYPE: ALBUM
47        PAGE SIZE: 8X10
48        ALBUM TYPE: 3 RING PUNCH - 2" THICK (50 PAGES)
49        BACKROUND STYLE: #217 - MARBLE
50        PAGE NUMBERS:
51            STYLE: - 1 -
52            FONT: HELVETICA
53            COLOR: BLUE
54            LAST PAGE NUMBER: 17
55        IMAGE NUMBERS: 1-6, 9-16
56        SHIP TO: DESIGNEE #2
57        STATUS: ORDERED, NOT YET FULFILLED
58
59    PRODUCT ID -2
60    PRODUCT TYPE: FRAMED PRINT
61        FRAME SIZE: 14X16
62        FRAME STYLE: #175 - CLASSIC - WALNUT
63        MATTE STYLE: #165 - TEXTURE - WOODGRAIN
64        IMAGE NUMBERS: 3
65        SHIP TO: DESIGNEE #2
66        STATUS: ORDERED, NOT YET FULFILLED
67
68    PRODUCT ID -3
69    PRODUCT TYPE: SERVICE PRINT
70        PRINT SIZE: 4X6
71        PRINT FINISH: GLOSSY
72        DATE STAMP: FRONT PRINT, LOWER LEFT, WHITE 12PT. HELVETICA
73        IMAGE NUMBERS: 1-18
74        SHIP TO: DESIGNEE #1
75        STATUS: ORDERED, NOT YET FULFILLED
76
```

FIG. 5B

| TIME SINCE UPLOAD | SAME DAY | <1 WEEK | <1 MONTH | <6 MONTHS | <2 YEARS | >2 YEARS |
|---|---|---|---|---|---|---|
| 4"X6" PRINT | $0.20 | $0.30 | $0.35 | $0.40 | $0.50 | $1.00 |
| 5"X7" PRINT | $0.60 | $0.80 | $1.00 | $1.20 | $1.50 | $3.00 |
| 8"X12" PRINT | $2.00 | $3.00 | $3.50 | $4.00 | $6.00 | $8.00 |
| 14"X16" PRINT | $8.00 | $10.00 | $12.00 | $16.00 | $20.00 | $30.00 |
| 4"X6" FRAMED PRINT | $5.00 | $5.50 | $6.00 | $6.50 | $7.00 | $8.00 |
| 5"X7" FRAMED PRINT | $8.00 | $9.00 | $10.00 | $11.00 | $12.00 | $15.00 |
| 8"X12" FRAMED PRINT | $12.00 | $14.00 | $15.00 | $16.00 | $18.00 | $20.00 |
| 14"X16" FRAMED PRINT | $20.00 | $22.00 | $24.00 | $26.00 | $30.00 | $35.00 |
| 5"X7" ALBUM PAGE | $3.00 | $3.50 | $4.00 | $4.50 | $5.00 | $6.00 |
| 8"X10" ALBUM PAGE | $5.00 | $5.50 | $6.00 | $6.50 | $7.00 | $8.00 |
| 10"X12" ALBUM PAGE | $8.00 | $8.50 | $9.00 | $9.50 | $10.00 | $12.00 |

FIG. 8A

| TIME SINCE UPLOAD | BASE PRICE |
|---|---|
| 4"X6" PRINT | $0.20 |
| 5"X7" PRINT | $0.60 |
| 8"X12" PRINT | $2.00 |
| 14"X16" PRINT | $8.00 |
| 4"X6" FRAMED PRINT | $5.00 |
| 5"X7" FRAMED PRINT | $8.00 |
| 8"X12" FRAMED PRINT | $12.00 |
| 14"X16" FRAMED PRINT | $20.00 |
| 5"X7" ALBUM PAGE | $3.00 |
| 8"X10" ALBUM PAGE | $5.00 |
| 10"X12" ALBUM PAGE | $8.00 |

| TIME SINCE UPLOAD | BASE PRICE | <1 WEEK | <1 MONTH | <6 MONTHS | <2 YEARS | >2 YEARS |
|---|---|---|---|---|---|---|
| MULTIPLIER | 1.00 | 1.20 | 1.30 | 1.40 | 1.60 | 2.00 |

FIG. 8B

PROVIDING A DISCOUNTED PAYMENT SCHEDULE FOR UTILIZING AND DELETING STORED IMAGES

CROSS REFERENCE TO RELATED APPLICATION

This application is a continuation of U.S. Ser. No. 09/730,703 filed Dec. 6, 2000, now U.S. Pat. No. 6,760,128.

FIELD OF THE INVENTION

The present invention relates to an effective method for a user to make payment for ordered services related to stored images by a service provider.

BACKGROUND OF THE INVENTION

The transfer of digital images from a user to a service provider for storage and printing is becoming more popular and more important. Typically, a digital camera user takes a plurality of digital images, which are stored on a removable memory card. These images can be transferred from the memory card and stored, for example, on a hard drive, recordable CD, or other non-volatile memory associated with the user's computer. While these stored images can be printed on a local printer, such as an ink jet printer, it is often simpler and less expensive for the user to have the images printed by a service provider. When services are ordered from a service provider, the images need to be uploaded using a channel such as the Internet, and temporarily stored. The uploaded images can be stored for long-term access via the Internet. The storage of these images represents a significant cost to the service provider, and users are often unwilling to pay a monthly fee to the service provider for this service.

Digital images from scanned photographic film can be uploaded to a service provider for viewing, as described in commonly assigned U.S. Pat. No. 5,666,215 to Fredlund et al., the disclosure of which is herein incorporated by reference. Using a web browser, a group of these digital images can be viewed and selected for printing, for example using the Kodak Photonet Service. The user can select the size of each print to be produced, and the quantity of prints to be made from each image. Album pages can be produced from digital images by arranging numerous images on the same page, as described in commonly assigned U.S. Pat. No. 6,004,061 to Manico et al., the disclosure of which is herein incorporated by reference. These album pages can be customized in terms of the size and arrangement of images on the page, the size and finish of the album pages, and the background color or patterns used. Another service that can be provided using digital images is producing digital storage media (e.g. CD-R discs) with duplicate copies of the digital images.

Some web sites, such as the site provided by OFOTO at www.ofoto.com, enable a user to upload a group of digital images for long term storage and sharing with others over the Internet, and for providing digital printing services. This site permits a user to obtain an account using his e-mail address as the account name, and to provide a password and address information. The user can then upload a group of images, which are stored by the service provider at no cost to the user. After all the images are uploaded, the user can select particular images for printing or sharing with third parties designated by the user. The user is charged a set fee for each print made, depending on the print size. The cost of each print is the same whether the image was stored by the service provider for only one day, or for many months or years. Therefore, the user has no incentive to order prints immediately upon uploading, and the service provider is not compensated for the long-term storage of the user's images.

SUMMARY OF THE INVENTION

It is an object of the present invention to provide an effective method for making payment for ordered services using images stored by the service provider.

This object is achieved by a method of selecting images from a plurality of images previously transferred from a user and stored by a service provider, and ordering services to be provided utilizing the images, comprising:

a) establishing an account for the user with the service provider to permit the user to have access to ordered services;

b) receiving a plurality of images from the user and storing the plurality of images in an electronic database provided by the service provider;

c) displaying image designators for at least a subset of the images for viewing by the user;

d) the user selecting a service to be provided using at least one selected image from the plurality of images stored in the electronic database, e) providing a price and a lower discounted price for the selected service; and f) using the discounted price if the user deletes at least one of the plurality of images from the electronic database.

It is an advantage of the present invention to provide a method for encouraging users of images stored by a service provider to utilize their images as soon as possible in order to get a reduction in the cost they must pay for the services provided.

It is a further advantage of the present invention to provide a method for compensating service providers for the costs associated with long-term storage of digital images.

It is a further advantage of the present invention to provide a method for obtaining digital printing services which provides a low initial cost to a user, and then stores the images at no cost to the user while providing an option to the user to obtain prints in the future, at a higher cost.

BRIEF DESCRIPTION OF THE DRAWINGS

FIG. 5 is a diagram depicting service account information including images and corresponding designated dates;

FIG. 8A and FIG. 8B illustrate two different payment schedules than can be used for the method of FIG. 2.

DETAILED DESCRIPTION OF THE INVENTION

The present invention provides an effective method for making payment for ordered services using images uploaded to a service provider on an earlier date. The images may be uploaded to the service provider over a channel, such as the Internet, using the method described in commonly assigned U.S. patent application Ser. No. 09/691,364, filed Oct. 18, 2000 to Berarducci, et. al., the disclosure of which is herein incorporated by reference. In the present invention, a designated date, typically the date on which the image was uploaded, is stored for each image, or alternatively for the group of images uploaded on a particular date. Either immediately, or at a later date, the transferred images may be used to produce photo products, such as standard photographic prints, framed photographic enlargements, complete album pages, PictureCD discs, or other photo products. The customer is billed for the photo products according to a payment schedule. The payment schedule provides different service charges for the same service when the service is ordered at different times relative to the designated date. For example, the cost of a particular size print is lower on the day the image is uploaded (e.g. $0.20), and increases in cost in subsequent months and years (e.g. increases by $0.02 per month), as the time between the current date and the designated date (e.g. the date the image was uploaded) becomes larger.

Figure 1A:
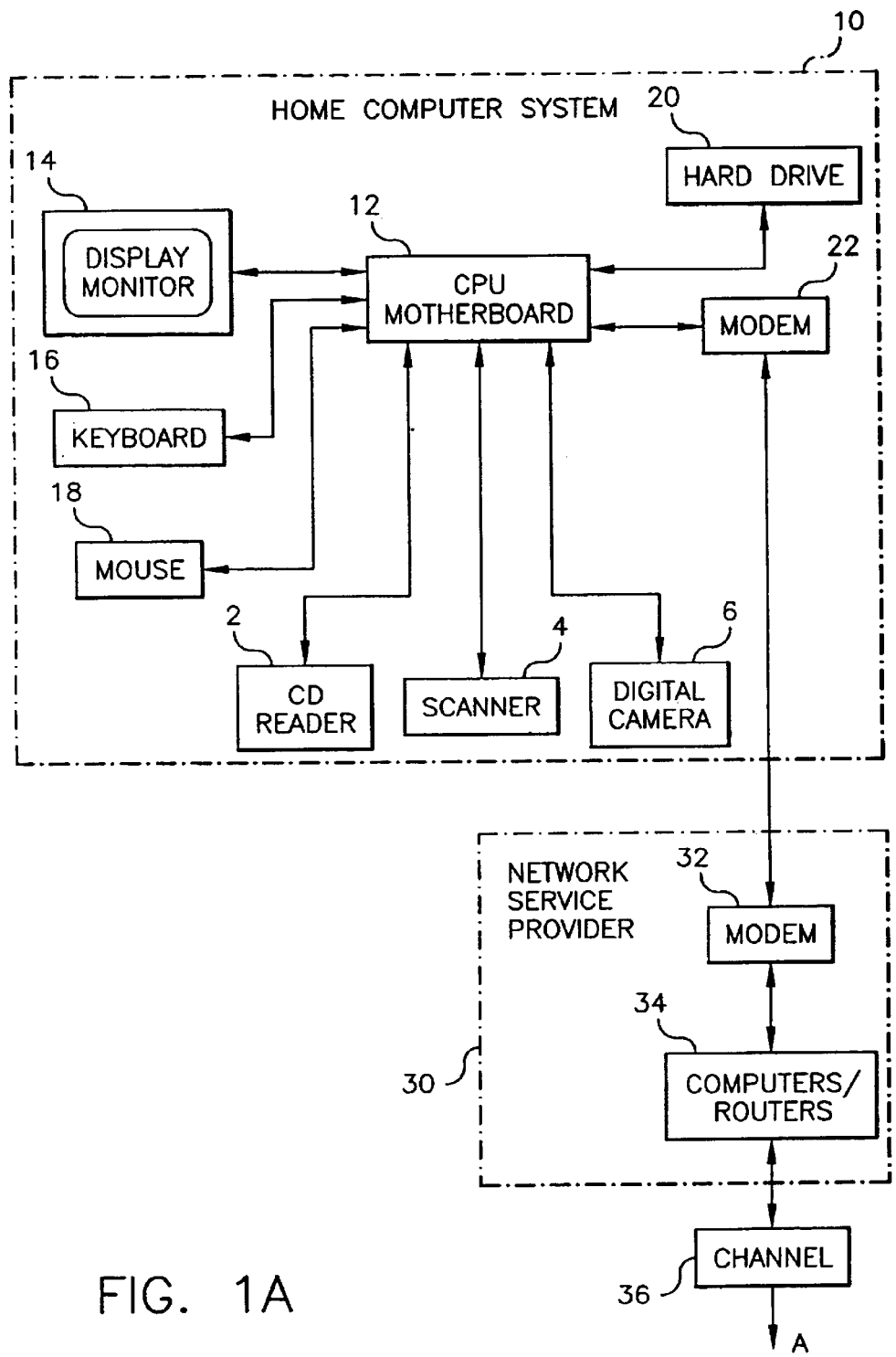
FIG. 1 depicts a block diagram of a system that implements this invention.
Figure 1B:
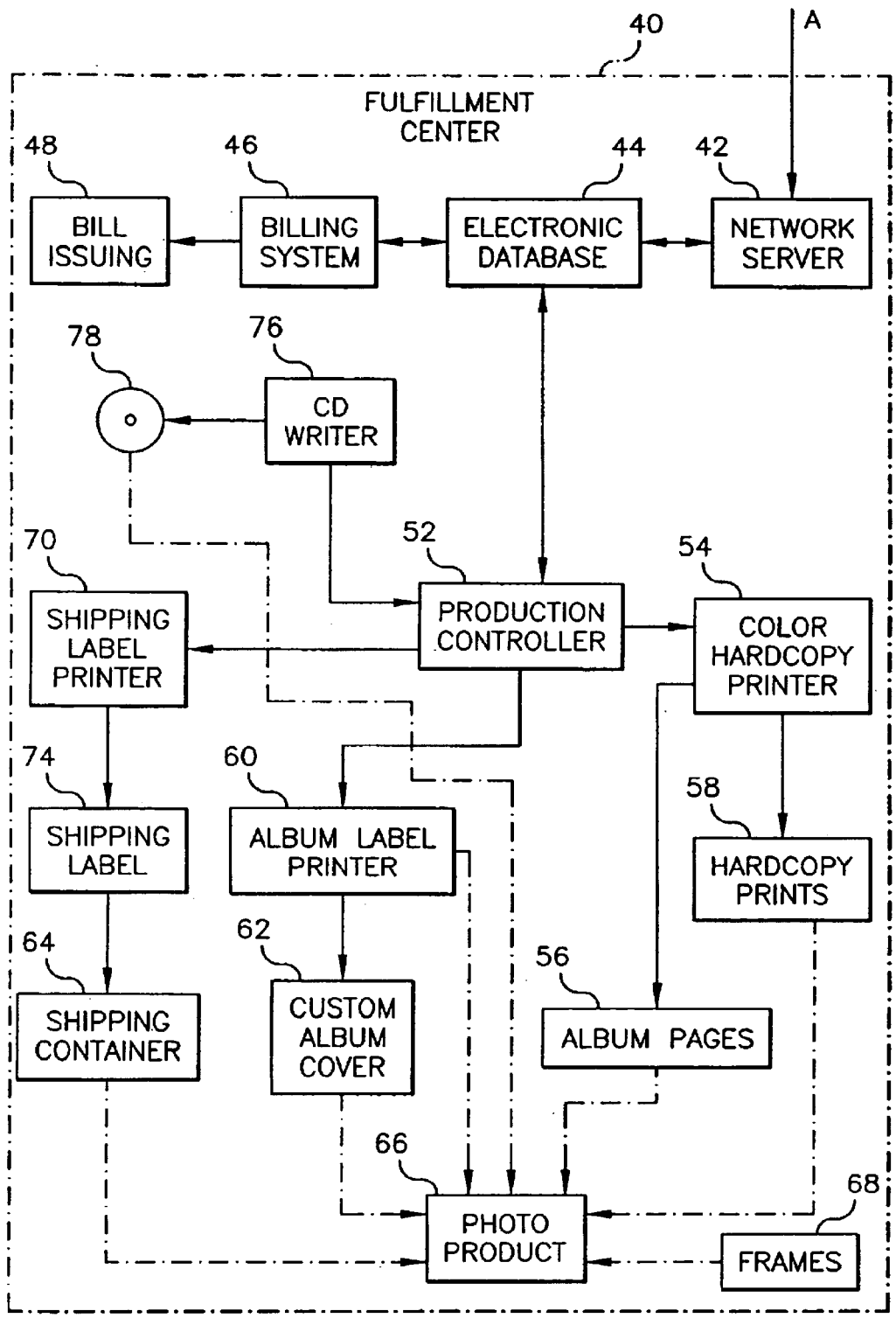

As shown in FIG. 1, the system includes a home computer system (with associated peripherals) 10 located at the customer location (e.g., the user's home). The home computer system 10 also includes equipment located at a network service provider 30, such as an Internet service provider (ISP), which communicates with the home computer system 10 to provide a network connection for the customer to a channel 36, such as the Internet. The system further includes a fulfillment center 40 which communicates with the home computer system 10 via the ISP 30 to perform the steps of transferring and selecting images, creating and shipping a photo product 66, and providing billing. The fulfillment center 40 includes an electronic database 44, which is located remote from the user's computer 10. It is understood that a system such as a game console, dedicated Internet appliance, set top box, or retail kiosk may be substituted for the home computer system 10.

The various portions of the fulfillment center 40 can be located in a single building or complex of adjacent buildings, or can be geographically dispersed over several sites in different cities or even different continents. For example, the electronic database 44 and the album production controller 52 can be provided by computers located in different cities and interconnected via a suitable digital communications network, such as the Internet. Furthermore, the electronic database 44 can itself be distributed over several computers in several different locations.

The home computer system 10, which can be, for example, a Dell Dimension XPS M200, includes a CPU motherboard 12, using, for example, a Pentium 200 MHz MMX processor as well as RAM memory. The CPU motherboard 12 executes software stored on a hard drive 20, for example, the well known Windows 98 operating system software and the Internet Explorer web browser software, both provided by Microsoft Corp. of Redmond, Wash. The CPU motherboard 12 is coupled to a display monitor 14 and a keyboard 16. A mouse 18 permits the customer to readily communicate with the CPU motherboard 12. The customer's computer 10 also includes a dial-in modem 22 for communicating with the ISP 30 in order to connect to a channel 36, such as the Internet.

The CPU motherboard 12 communicates with a color scanner 4, such as a Microtek ScanMaker E6, which can scan color photographs (not shown) and store digital images of the photographs on the hard drive 20. The CPU motherboard 12 also communicates with a CD reader 2. The CD reader 2 can be used to input digital images from a CD-R disc, such as a Kodak PictureCD (not shown). The CPU motherboard 12 also communicates with a digital camera 6 via a suitable interface, such as the well known USB or RS-232 serial interfaces. The digital camera 6, for example a Kodak DC280 Zoom digital camera, can be used to provide digital images. The digital images provided by the CD reader 2, scanner 4, and digital camera 6 can be uploaded from the home computer system 10 to the fulfillment center 40 via ISP 30 and channel 36.

The ISP 30, for example, Earthlink Network, Inc. of Pasadena, Calif., includes banks of modems 32, one of which is connected to communicate with the modem 22 of the customer's computer 10. The modem 32 in turn communicates with computers/routers 34 in order to provide a connection to the channel 36 using equipment and techniques well known to those skilled in the art.

The fulfillment center 40 is connected to the channel 36, such as the Internet, by a network server 42, such as an Internet server, which is comprised of one or more computers and associated peripherals. The fulfillment center 40 is normally owned or controlled by the service provider. The electronic database 44 provides information describing numerous photo product options, including printing a group of digital images onto album pages. The electronic database 44 can be contained on the same computer as the network server 42, or can utilize a separate computer, or can be distributed over several computers at the same physical site, or at different sites.

The electronic database 44 includes information describing different features of the albums and other photo products 66 that can be selected and customized by the customer at the remote location, using the customer's computer 10. The electronic database 44 also includes information describing photo product options, for example album features such as providing various background colors or textures, page numbers, page captions, image captions, etc. The album pages can be bound in a cover, or can include holes to permit the pages to be inserted into a standard binder, such as a three-ring binder. These album feature options can be demonstrated via software programs, for example, JAVA applets, MPEG or QuickTime movies, or Shockwave files, which depict the functionality of features that the customer can choose. The electronic database 44 also stores the payment schedule to be described later in reference to FIG. 8.

When a photo product 66 is purchased by the user, the electronic database 44 communicates with a billing system 46 to verify that the payment identifier (e.g., credit card or debit card number) provided by the customer is valid, and to debit the account for the purchase. As shown in block 48, the bill is issued. The customer's account that is debited can, of course, be located at a remote financial institution. Typically, as with credit cards, this financial institution will make payment to the direct provider or seller of shippable photo product 66. This is generally done by wiring the amount into the service provider's account, generally an account established with another financial institution.

As shown in FIG. 1, the electronic database 44 is connected to production controller 52. The production controller 52 controls one or more color hardcopy printers 54, which can produce album pages 56 or separate hardcopy prints 58. The hardcopy prints can be placed in frames 68. The production controller 52 is also connected to a CD writer 76, which can produce PictureCDs 76 having digital images and application software for using the digital images. The production controller 52 can optionally be connected to devices (not shown) for producing t-shirts, coffee mugs, etc. incorporating one or more images uploaded by the user. The production controller 52 is also connected to an album label printer 60 which produces labels that can be attached to a standard album cover to provide custom album cover 62.

The electronic database 44 also provides long-term storage of the uploaded images. In this embodiment, stored images are accessible (e.g. viewable) via the Internet by authorized users, as described, for example, in commonly assigned U.S. Pat. No. 5,760,917 to Sheridan, the disclosure of which is herein incorporated by reference.

The production controller 52 also controls a shipping label printer 70 to produce a shipping label 74. The shipping label 74 is attached to a shipping container 64 (e.g., a cardboard box containing packing material) that contains and protects the photo product 66 during shipment (e.g., via air express mail, ground carrier, etc.) to the customer or the customer's designee.

Figure 2A:
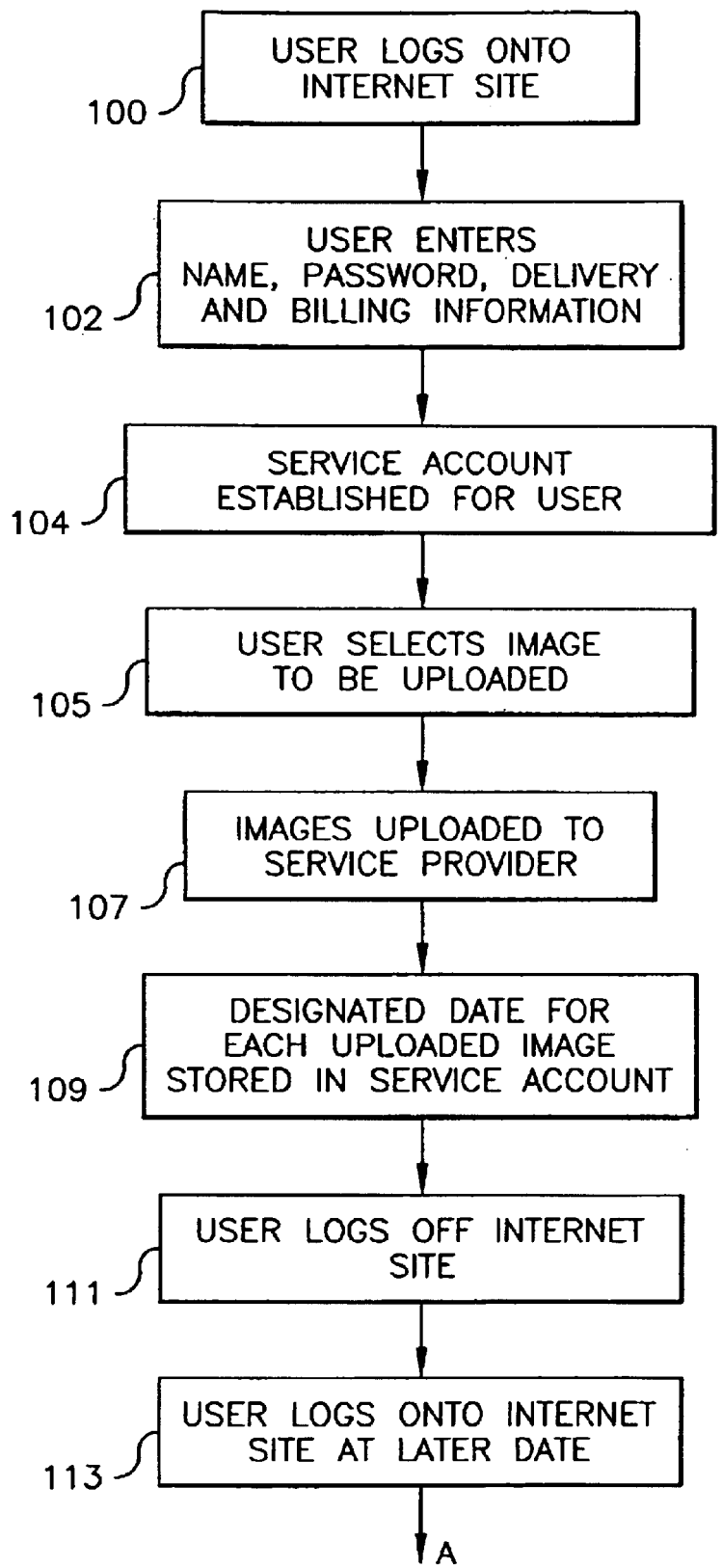
FIG. 2 is a flow diagram of a method that implements this invention.
Figure 2B:
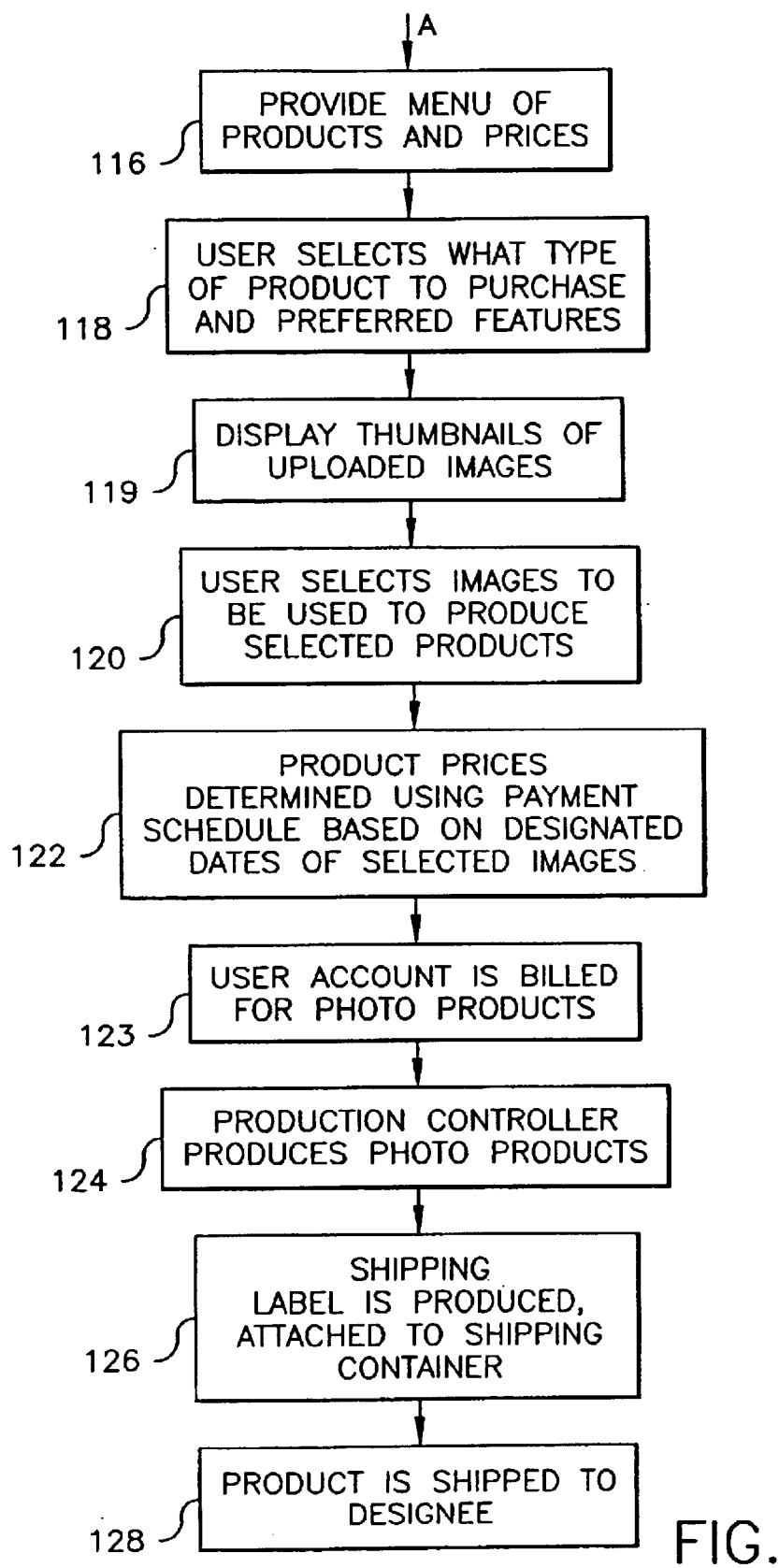

Turning now to FIG. 2, there is shown a flow diagram of a typical method for effectively transferring images from a user to a service provider to produce photo products 66, such as prints, albums, PictureCDs, etc. As shown in block 100, the user (i.e. the customer), using a digital communication network, logs onto the channel 36, which can be the Internet. The user can, of course, use a service provider, such as the ISP 30, to gain access to the channel 36. The ISP 30 uses an address, such as an Internet protocol (IP) address, to establish a connection between the user's computer 10 and a product provider or seller who owns or controls the fulfillment center 40.

In block 102, the user enters their name, selects a password, and provides delivery and billing information. This information identifies the user and one or more designees (e.g. a person to whom the photo product 66 should be shipped, which can of course be the user). It includes addresses of both the user and the user's designees. The user also identifies an account to be debited to pay for the photo product(s) to be purchased. Often this will be a credit card having a payment identifier that specifies the account of the customer to be charged or debited. Frequently, this will be in a financial institution. The payment identifier can be a credit card number that specifies a particular credit card account. As used in this specification, a credit card will also include a debit card.

In block 104, a user service account is established for the user. The information stored in the service account includes the information entered by the user in block 102. This service account information will later be augmented by additional information providing an image identifier and designated date for each uploaded image, and the photo product options selected by the customer. FIG. 5 provides an example of the service account information. The billing information (e.g. credit card number) and other sensitive information provided in the service account can be encrypted to prevent discovery and unauthorized use. The service account information is preferably stored as part of the electronic database 44 in the fulfillment center 40. Alternatively, it is possible for some of the service account information to be stored in the customer's computer 10, for example on the hard drive 20, and communicated to the fulfillment center 40 as required.

In block 105 of FIG. 2, the customer selects images to be uploaded from the home computer 10 to the fulfillment center 40, in order to be stored by the service provider, and possibly utilized in the future to produce one or more photo products. In a preferred embodiment, the CPU 12 displays on the display monitor 14 a display screen 400 as shown in FIG. 7. The display screen 400 includes a two-dimensional array of thumbnail images 402 obtained from the digital camera 6, the CD reader 2, or the hard drive 20. The thumbnail images 402 preferably are thumbnail images stored within the Exif/JPEG image files provided by the digital camera 6, to be described later in reference to FIG. 6. The user selects all of the images, or a subset of the images, by clicking the mouse 18 on the "select all" icon 432, or on any number of thumbnail images 402. FIG. 7 shows that four thumbnail images 402a, 402b, 402c, and 402d (which are outlined) have been selected.

In order to select desired images from a large number of thumbnail images 402, arrow controls 404 on the right portion of display screen 400 enable the user to scroll through the larger number of thumbnail images 402 to view a group of the thumbnail images 402 (e.g., 15 thumbnail images) at a time. The user can then select additional images to be uploaded by clicking the mouse 18 on any number of thumbnail images 402.

As the user selects images, an optional image data upload indicator 406 displays the number of images selected for uploading 408 (e.g. 27 images), as well as other information such as the total size of all of the selected files 410 (e.g. 12.1 Mbytes total for all selected images) and the estimated time for image uploading 412 (e.g. 50 minutes) given the data rate of the user's modem 22 (e.g. 32 kbit/sec average net upload speed).

In block 107, the digital images are uploaded to the service provider over the channel 36. As described in co-pending U.S. patent application Ser. No. 09/691,364, filed Oct. 18, 2000 to Berarducci, et. al., the disclosure of which is herein incorporated by reference, cited earlier, the images may be uploaded at a more effective time (e.g. at night) rather than immediately after they are selected by the user. The uploaded images are stored at the fulfillment center 40 in the electronic database 44.

In block 109, the image identifiers corresponding to each of the customer's uploaded images, and the designated date indicating the date the image was uploaded, are added to the user's service account information. The image identifier can be the file name of the uploaded image. Alternatively, the image identifier can be a complete pathname specifying the storage device and the directory structure needed to locate each image in the electronic database 44. Alternatively, the image identifier can be data string which matches a data string within the corresponding image file, such as an GUID (globally unique ID), an image number, an image title, or the like. The designated date can be the exact time and date of uploading. Alternatively, it can be less precise, such as the date, the week and year, the month and year, or the year the image was uploaded. Alternatively, the designated date can be the date the image was photographed, if the date is automatically recorded within the image file by the digital camera, as will be described later in reference to FIG. 6. Alternatively, the designated date can be the date the film containing the image was scanned by the user or by a service provider. Instead of (or in addition to) being stored in the user service account, the designated date can be stored within the image file itself, for example using a TIFF tag, such as the Image Description tag within the Exif application segment 1 of the uploaded Exif/JPEG file.

In block 111, the user logs off the Internet site. Alternatively, the user may remain on the Internet site and immediately order products to be produced using the uploaded images, as will be described in relation to blocks 116 to 128. In block 113, the user logs onto the Internet site of the service provider at some later time, to order photo products using the images uploaded in block 107.

Figure 3:
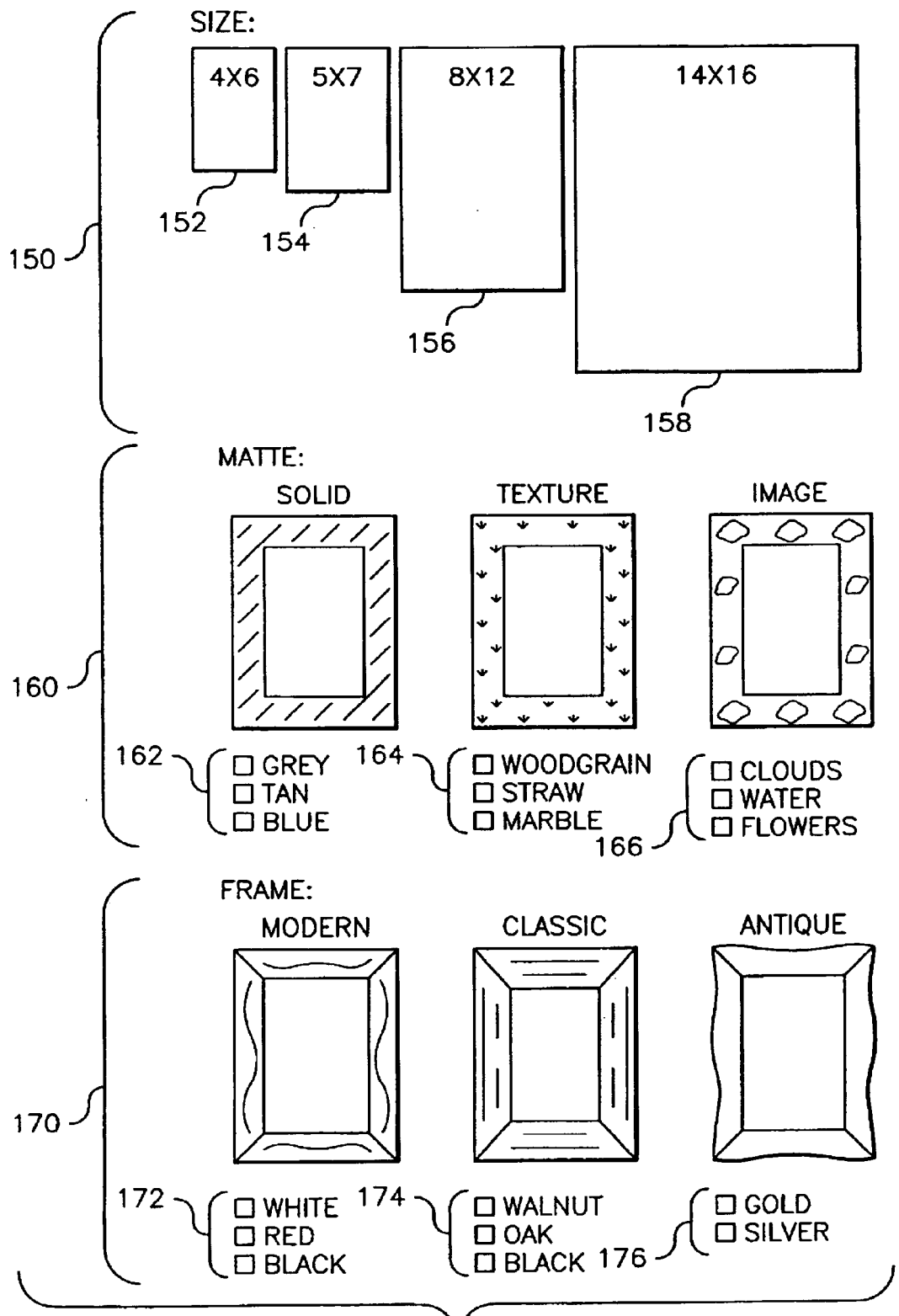
FIG. 3 depicts a selection of print sizes, picture frame styles, and picture frame mattes provided by the system of FIG. 1.
Figure 4:
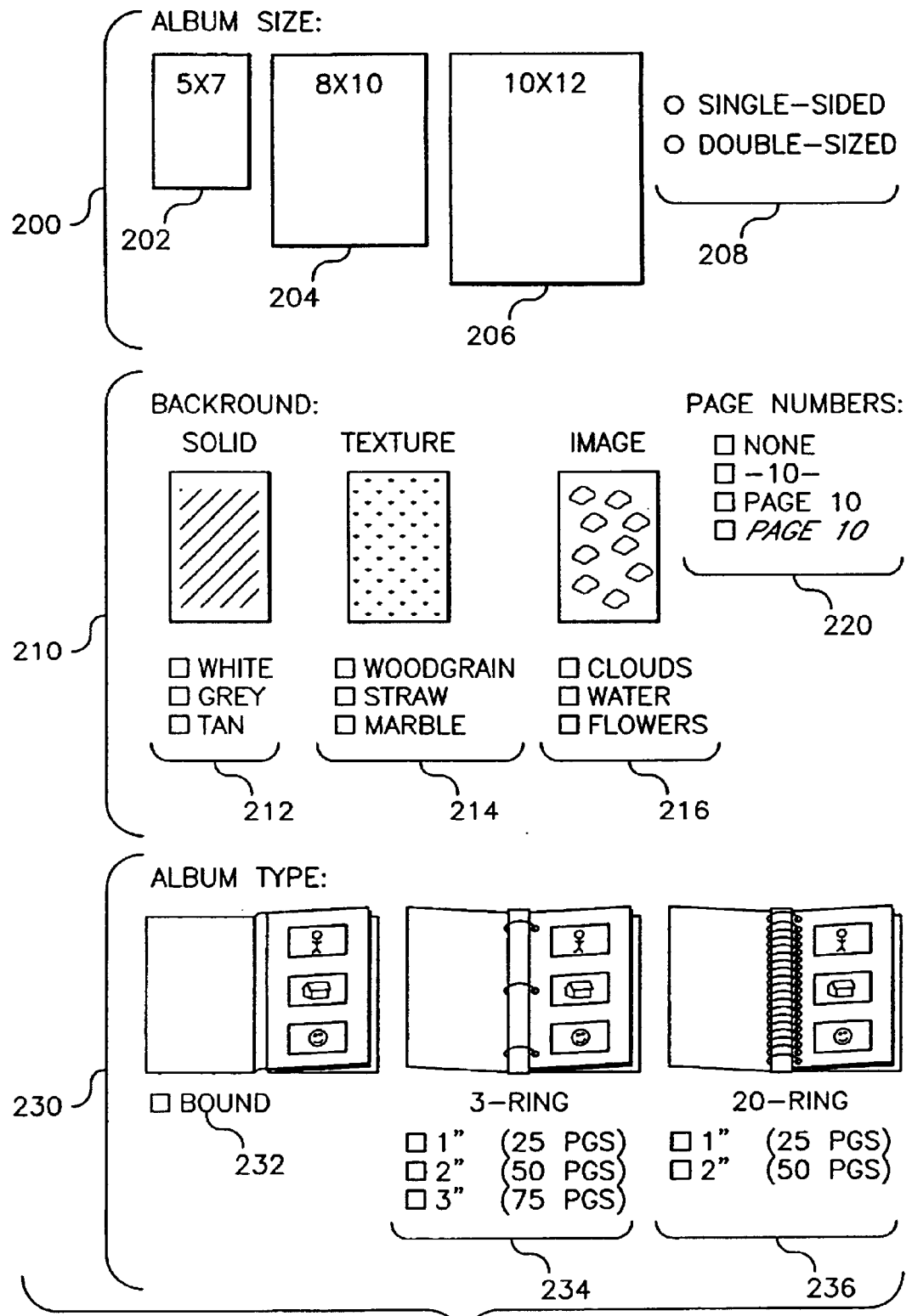
FIG. 4 depicts an album page that can be provided by the system of FIG. 1.

In block 116, the fulfillment center 40 provides the customer with a menu of photo products 66 that are available for customization and purchase, such as standard service prints, framed hardcopy prints as depicted in FIG. 3, and customized photo albums as depicted in FIG. 4. The fulfillment center can also provide a menu of customizable features for the type of product selected by the user. In block 118 the customer selects what type of products (e.g. standard service prints, framed hardcopy prints, customized photo albums, PictureCD, etc.) to purchase. The user can also select preferred features to customize the selected photo product, from a list of options.

The options for standard prints include providing the prints in various sizes (e.g. 3"×5", 4"×6", etc.) and various surface finishes (e.g. glossy, matte finish, etc.). The standard prints can also include text, such as the date the picture was captured or printed. The date the pictures were captured can be obtained from the digital image file to be uploaded, if the picture was taken by a digital camera or by an APS film camera having a real-time clock. The user can select whether or not to include this date stamp, where to position the text (e.g. on the front at the lower left, or on the back of the print.). The user can also select the color (e.g. white or yellow) and the font (e.g. Helvetica or Script) for the date stamp.

FIG. 3 depicts framed options that can be selected by the user. The options include selecting the size of the print from a plurality of print sizes 150, including 4"×6" size 152, 5"×7" size 154, 8"×10" size 156, and 14"×16" size 158. The user selects the size by selecting the appropriate print size icon (e.g. icon 152, 14, 156, or 158). The options also include selecting a matte style from a plurality of styles 160, including solid mattes 162 in gray, tan, and blue, textured mattes 164 in woodgrain, straw, or marble, and background image mattes 166 including clouds, water, or flowers. The user selects the matte by selecting the appropriate radio button (e.g. one of buttons 162, 164, or 166) for their preferred matte style. The user then selects a picture frame style from a variety of styles 170, including modem styles 172 in white, red, and black, classic styles 174 in walnut, oak, and black, and antique styles 176 in gold and silver. The user selects the picture frame style by selecting the appropriate radio button (e.g. one of buttons 172, 174, or 176) for their preferred frame style. Of course, many more size, matte, and frame options can be presented to the user using various types displays, such as pull-down menus, scroll bars, etc. The selected combination of print size, matte style and frame style is then presented to the user. For example, if the user selects a classic walnut frame with a texture wood grain matte, the Internet server 42 would present to the user an image depicting this combination for the user to review.

FIG. 4 depicts album options that can be selected by the user. The options include selecting the size of the album from a plurality of sizes 200, including 5"×7" size 202, 8"×10" size 204, and 10"×12" size 206. The user selects the size by selecting the appropriate print size icon (e.g. icon 202, 204, or 206). The options also include using radio buttons 208 to select single-sided pages (e.g. print only on 1 side of the album page) or double-sided pages. The options further include selecting a preferred background style from a plurality of styles 210, including solid backgrounds 212 in white, gray, or tan, textured backgrounds 214 in wood grain, straw, or marble, and background images 216 including clouds, water, or flowers. The user selects the background style by selecting the appropriate radio button (e.g. one of buttons 212, 214, or 216). The user then selects whether to include a page number from a plurality of options using radio buttons 220. The options include no page numbers and several different styles of page numbers. The color, size, and font of the text used for the page numbers and image captions could also be selected using a separate menu (not shown). Finally, the user selects an album type from a plurality of album types 230. The album type is selected by the user by selecting one of the radio buttons for bound albums 232, 3-ring albums 234 (including 1", 2", and 3" thick 3-ring albums) or 20-ring albums 236 (including 1" and 2" thick albums). Of course, many more size, background, and album type options can be presented to the user using various types displays, such as pull-down menus, scroll bars, etc. The selected combination of album size, background, page numbers, and album type is then presented to the user. For example, if the user selects 8"×10" double-sided album pages in a 3-ring, 2" thick binder with a marble texture background and a particular page number style, the internet server 42 presents to the user an image depicting this combination for the user to review.

In block 119, the network server 42 transfers image designators for the images uploaded earlier by the user (e.g. uploaded in block 107) from the electronic database 44 to the home computer system 10 via the channel 36 and the network service provider 30. The image designators are preferably thumbnail image files provided using the thumbnail image data stored within the Exif/JPEG files produced by the digital camera 6, as will be described later in relation to FIG. 6. These thumbnail images are then displayed on the display monitor 14 of home computer system 10, so that the user can select the images to be utilized in the photo product selected in block 118. The display can be similar to the display screen 400 shown in FIG. 7, but without the upload indicator 406. In place of the upload indicator, a "selected images indicator" (not shown) can be used to display the total number of images selected, and the total cost for which the user will be billed, to be calculated as will be described in relation to block 122. Alternatively, the image designators may be the file name of the uploaded files (e.g. DCP_0012.JPG) or may be a title provided by a user at an earlier date (e.g. "Matthew, age 3, at the White Sands of Dover") and stored within the image file, for example in the Image Description tag within the Exif/JPEG file, prior to uploading.

In block 120, the user selects the images to be used to produce the photo products they have selected. The selection is accomplished using the mouse 18 or keypad 16 to identify appropriate images. This can be done as described earlier in relation to FIG. 7.

Information describing the products selected by the user can be stored in the service account information depicted in FIG. 5. As shown in the example depicted in FIG. 5, the service account information includes the user name, password, user e-mail address, user shipping address, and billing information (lines 3–7). Some or all of this information may be encrypted for security reasons. The service account information can also include the shipping addresses for one or more designees (lines 9–11). This information is stored in the service account during block 105 described earlier.

The image list (lines 13–42) in the service account information provides a list of image identifiers (e.g. image names) and designated dates for each of the images that were uploaded from home computer system 10 to fulfillment center 40 and stored in electronic database 44 uploaded. The upload list provides a reference number (e.g. Image 1), an image name (e.g. DCP_0012.JPG) and an upload date (e.g. 14/01/1999 for Jan. 14, 1999). In the example of FIG. 5, a large number (more than 600) images have been uploaded, but only a few of the image list entries are shown. The image list information is stored in the service account during block 107 described earlier.

The service account information can also provide information defining the products selected by the user. In the example of FIG. 5, several products having different identifiers (ID) such as Product ID-1 (lines 45–57) which specifies a customized album, Product ID-2 (lines 59–66) which specifies a framed print, and Product ID-3 (lines 68–75) which specifies customized service prints. The album related information (lines 45–57) includes the page size, album type, and background style selected. It also includes page number information, such as the style, font, and color of the text, and the last page number printed. The last page number information is updated each time new album pages are printed. It can be used to automatically tell the user when an album has been filled, and a new album needs to be purchased. The album related information also includes a list of image numbers (line 23) to be included in the album. These image numbers correspond to image identifiers listed in the Image list section (lines 13–42). The album related information also indicates that designee #2 should receive the order (line 56), and provides the order status (line 57). The order status indicates that this photo product has been ordered by the user, but not yet fulfilled (e.g. not yet produced and shipped). Once fulfilled, the status will be updated to indicate that this order has been completed.

The framed print information (lines 59–66) specifies the frame size, frame style and color, and matte style. It also includes a list of image numbers (line 64) to be used to produce the framed print. This image number (Image number 3) corresponds to the image identifier listed for image number 3 in the Image list section (line 16), which is the image identified as DCP_0017.JPG. The information also indicates that designee #2 should receive the order (line 65) and the order status (line 66).

The service print information (lines 68–75) specifies the print size, print finish, and the location, font style, size, and color of the date to be overlaid in the print. It also includes a list of image numbers (line 73) to be printed. The information also indicates that designee #1 should receive the prints (line 74) and the order status (line 75). The service print information could also specify other text or graphics selected by the user that should be added to the images when they are printed.

The service account information is stored in electronic database 44. Alternatively, some or all of the service account information could instead stored on hard drive 20, or could be duplicated on hard drive 20 of home computer system 10.

In block 122, the designated date for each image to be used in creating the photo product is determined, and used, along with other factors such as the type of photo product, to determine the price of the photo product selected by the user. The price is determined using a payment schedule that depends upon the designated date that the selected image was received. Two example payment schedules are shown in FIG. 8A and FIG. 8B. The designated date is determined from the service account information stored in block 109. The difference between the designated date and the current date is then determined. Since the designated date is typically the upload date, this difference is typically the "Time since upload".

In FIG. 8A, the payment schedule provides different prices for different products, as is typical in the prior art. However, unlike the prior art, it also provides different prices for different designated dates, as indicated by the "Time since upload" value. For example, a 4"×6" print costs only $0.20 if ordered on the date it was uploaded, when the order date is the same as the designated date. But the cost increases to $0.30 if the print is ordered later in that same week. If the print is ordered later in that same month, the price increases to $0.35. If the print is ordered after the first month, but before the end of the $6^{th}$ month after uploading, the price increases to $0.40. If the print is ordered after the end of the sixth month, but before the end of the $2^{nd}$ year after uploading, the price increases to $0.50. If the print is ordered after the end of the second year, the price increases to $1.00. The payment schedule shown in FIG. 8A further shows that the prices of other photo products (e.g. 5"×7" prints, 8"×12" framed prints, 10"×12" album pages, etc.) likewise increases as the "time since upload" increases, but not necessarily by the same percentage.

The alternative payment schedule shown in FIG. 8B provides different "Base" prices for different products, as is typical in the prior art. However, unlike the prior art, it also provides a "multiplier" which is a function of the designated date. The multiplier increases as the difference between the order date and the designated date increases, as indicated by the "Time since upload" columns. For example, the Base price of a 4"×6" print is $0.20. The multiplier for photo products ordered the same day they are uploaded is 1.0, so the price is $0.20. The multiplier for photo products ordered after the first day, but before the end of the first week since uploading is 1.20. Thus, the price for a 4"×6" print is 1.20 ×$0.20, or $0.24. The multiplier increases at the end of the first week to 1.30, increases again at the end of the first month to 1.40, increases again at the end of 6 months to 1.60, and increases at the end of two years to 2.00.

The payment schedules shown in FIG. 8A and FIG. 8B use 6 different "designated date" related increments: "same day" (ordered the same day as the image was uploaded), "<1 week" (ordered more than one day but less than one week after uploading), "<1 month" (ordered more than one week but less than one month after uploading), "<6 months" (ordered more than one month but less than six months after uploading), "<2 years" (ordered more than six months but less than two years after uploading), and ">2 year" (ordered more than two years after uploading). Of course, a different number of designated date related increments could be used. As one example, only two different increments, "immediately upon uploading" and "at least one day after uploading" could be used. In this case, one price is used when the photo product is ordered immediately after uploading, and a higher price is used when the photo product is ordered at any later date. As a second example, a continuous function could be used to determine the multiplier described in reference to FIG. 8B. One example function is:

$$\text{Multiplier} = 1.01 \times ((\text{order date}) - (\text{designated date}))$$

In this example, the price of the photo product increases by the same increment (1%) each day.

In some embodiments, the user can be sent an e-mail reminder a few days before the payment schedule is adjusted upward, suggesting that they order prints of particular images at the lower price, before the price increases. For the example payment schedule shown in FIG. 8A, the user is sent an e-mail notice when the "Time since upload" for any images becomes one week less than two years. The user is reminded that they may order photo products for a low price (e.g. $0.50 for a 4"×6" print) only for the next week, and that the price will be higher (e.g. $1.00 for a 4"×6" print) at the end of the week. Of course, the user may be given a further discount for ordering photo products within the next week, as a further incentive. The user may also be given a discount for deleting some number of unwanted images (e.g. 5 images) from their account prior to ordering photo products. This reduces the cost of image storage incurred by the service provider.

In block 123, the customer account provided in the service account information (FIG. 5) is billed for the order. The bill reflects the price of the photo products determined from the payment schedule described in relation to block 122. At this point, the financial institution having the customer's account designates such funds for transfer to the service provider.

In block 124, the production controller 52 produces the customized photo products using the uploaded images and the service account information (see FIG. 5) stored in electronic database 44. If the user has ordered an album, the uploaded digital images can be automatically arranged on the pages and printed by color hardcopy printer 54 to produce album pages 56 as described in commonly assigned U.S. patent application Ser. No. 09/347,310, filed Jul. 2, 1999 to Loui et al.; U.S. patent application Ser. No. 09/199,724, filed Nov. 25, 1998 to Shaffer et al; and Ser. No. 09/199,639, filed Nov. 25, 1998 to Shaffer et al., the disclosures of which are herein incorporated by reference. The last page number (line 54) in the service account information provided in FIG. 5 is updated to reflect the number of album pages that will be produced to complete the current order. Alternatively, as part of block 120, the user can manually arrange the images on the pages and also select preferred colors, messages, logos, or images for the custom album cover 62.

If the user has ordered framed prints, the digital images are printed using color hardcopy printer 54 to produce hardcopy prints 58. Each hardcopy print 58 includes the user selected matte border, for example the texture—wood grain border specified in line 63 of FIG. 5. Each hardcopy print 58 is then framed using the appropriate frame 68, for example the classic—walnut frame specified in line 62 of FIG. 5. If the user has ordered service prints, the digital images are printed using color hardcopy printer 54 to produce hardcopy prints 58. The hardcopy prints 58 use the size and finish specified in lines 70–71 of FIG. 5. Before printing, each digital image is overlaid with the date stamp as specified in line 72 of FIG. 5. If the user has ordered one or more PictureCDs using the uploaded images, the PictureCDs 78 are produced using CD Writer 76.

In block 126, the production controller 52 in FIG. 1 controls the shipping label printer 70 to produce the shipping label 74 using the shipping address of the customer or customer's designee provided in the service account information (see FIG. 5). The shipping label 74 is attached to the shipping container 64 that is used to ship the photo product 66.

In block 128, the photo product 66 incorporating the first group of digital images is delivered to the customer or the customer's designee. The term "delivery" means that the photo product 66 can be shipped to the customer or the customer's designee by the U.S. Postal Service (USPS) or by a carrier service, such as the United Parcel Service (UPS) or Federal Express. Alternatively, the photo product 66 can be delivered to a location such as the store where the retail kiosk 80 is located, where the customer can pick it up. In this case, the billing provided in step 123 can be delayed until the customer picks up the photo product 66, and the customer can then pay for the photo product 66 using cash, check, or a charge/debit card.

At a future time, the user may again return to the home computer system 10, log onto the Internet site, and enters their name and password. Alternately, the home computer system 10 can include a "cookie" created and stored on hard drive 20 when the user first accessed the Internet site in step 100. This "cookie" can automatically identify the user account. In response, the network server 42 accesses, from the electronic database 44 in FIG. 1, the service account information for the customer. In addition to ordering more photo products, the user can select another set of images to be uploaded from home computer 10 to fulfillment center 40, as described earlier in relation to block 105. As in block 105, this can be done by selecting to upload all the images from a particular CD inserted in CD reader 2 or stored in digital camera 6 or by individually selecting images to be uploaded. The service account information (FIG. 5) is updated to list the newly uploading images, including the date each image was uploaded.

The user will, of course, return to the Internet site of the service provider many times in the future to upload additional images and to order additional photo products. The product ID information stored in the service account information in FIG. 5 enables the user to simply and easily obtain similarly customized photo products, as described in commonly assigned U.S. patent application Ser. No. 09/576,288, filed May 23, 2000 to Parulski, the disclosure of which is herein incorporated by reference.

Figure 6:
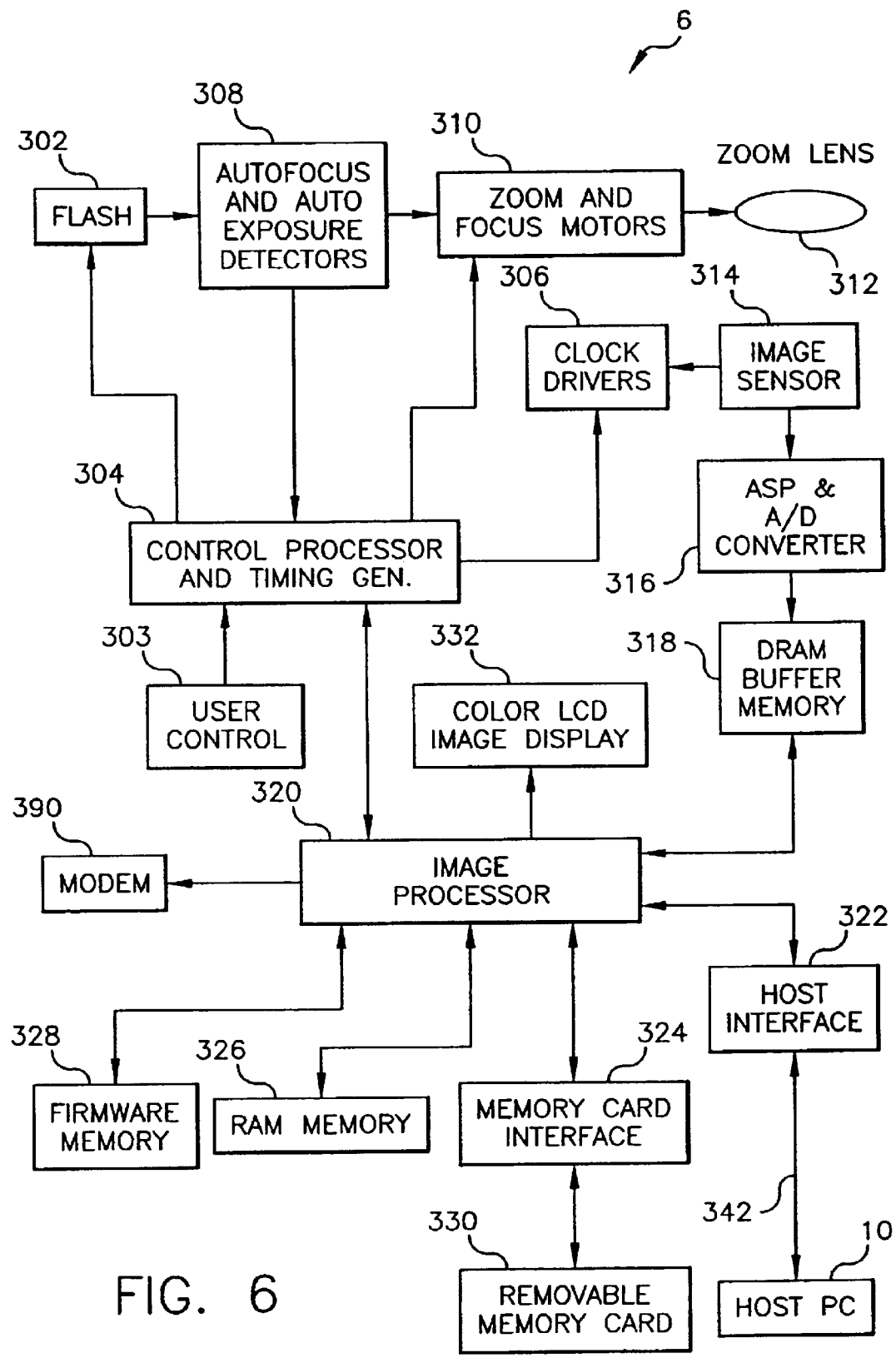
FIG. 6 depicts in more detail a digital camera shown as a block in FIG. 1.
Figure 7:
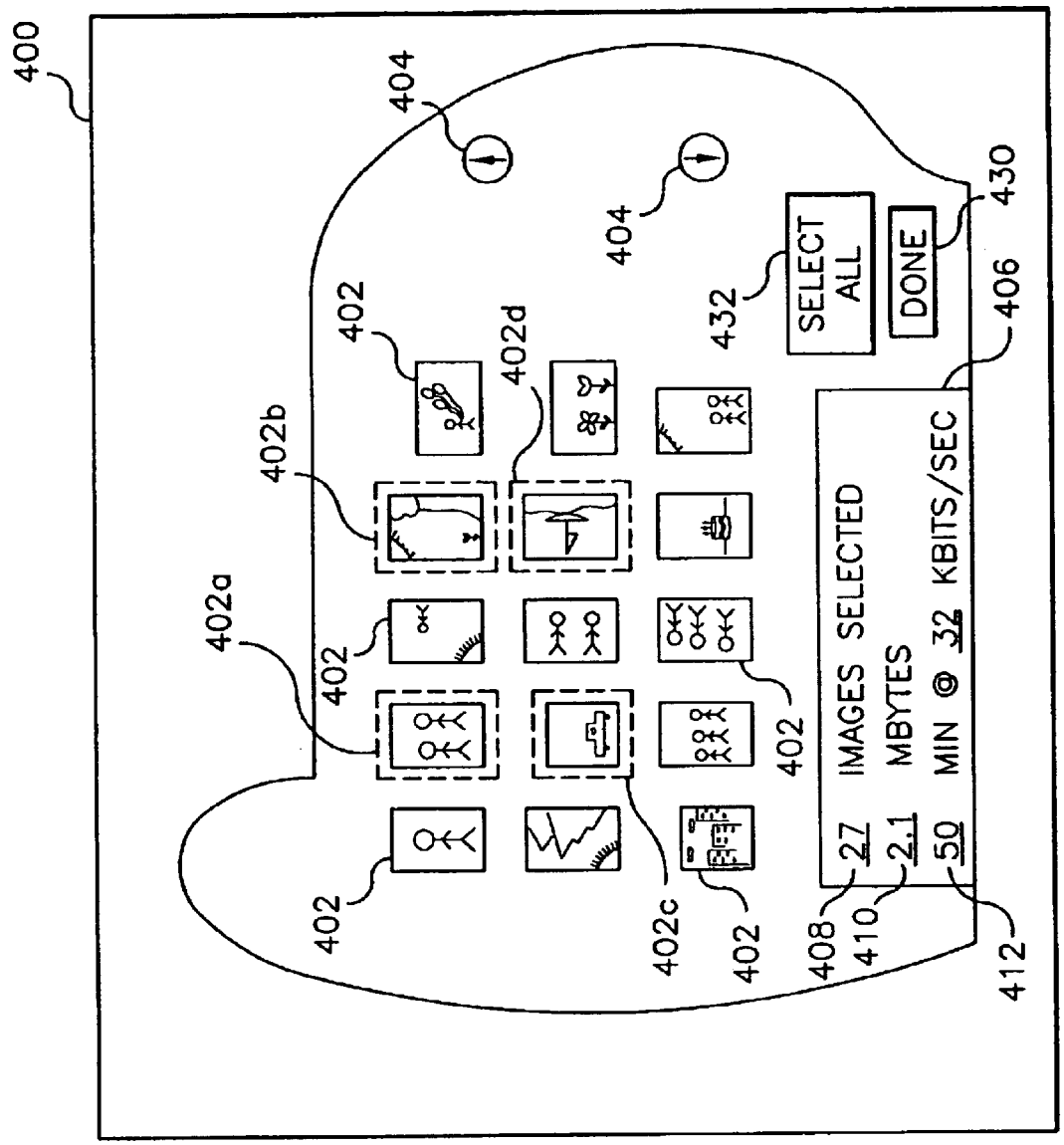
FIG. 7 is a graphical user interface screen to enable a user to select images to be uploaded.

FIG. 6 is a block diagram showing the electronic camera 6 in more detail. The electronic camera 6 produces digital images that are stored on the removable memory card 330. The electronic camera 6 includes a zoom lens 312 having zoom and focus motor drives 310 and an adjustable aperture and shutter (not shown). The zoom lens 312 focuses light from a scene (not shown) on an image sensor 314, for example, a single-chip color CCD image sensor, using the well known Bayer color filter pattern. The image sensor 314 is controlled by clock drivers 306. The zoom and focus motors 310 and the clock drivers 306 are controlled by control signals supplied by a control processor and timing generator circuit 304. The control processor and timing generator 304 receives inputs from autofocus and autoexposure detectors 308 and controls a flash 302. The analog output signal from the image sensor 314 is amplified and converted to digital data by the analog signal processing (ASP) and analog-to-digital (A/D) converter circuit 316. The digital data is stored in a DRAM buffer memory 318 and subsequently processed by a processor 320 controlled by the firmware stored in the firmware memory 328, which can be flash EPROM memory.

The processed digital image file is provided to a memory card interface 324 which stores the digital image file on the removable memory card 330. Removable memory cards 330 are known to those skilled in the art. For example, the removable memory card 330 can include memory cards adapted to the *CompactFlash Specification Version* 1.3, published by the CompactFlash Association, Palo Alto, Calif., Aug. 5, 1998. Other types of removable memory cards, or other type of digital memory devices (such as magnetic hard drives, magnetic tape, or optical disks) could alternatively be used to store the digital images.

The processor 320 performs color interpolation followed by color and tone correction, in order to produce rendered sRGB image data. The rendered sRGB image data is then JPEG compressed and stored as a JPEG image file on the removable memory card 330. The JPEG file uses the so-called "Exif" image format defined in "Digital Still Camera Image File Format (Exif)" version 2.1, July 1998 by the Japan Electronics Industries Development Association (JEIDA), Tokyo, Japan. This format includes an Exif application segment that stores particular image metadata, including the date and time the picture was captured, the lens f/number and other camera settings. The date and time are determined from a real-time clock (not shown) provided by control processor 304.

The processor 320 also creates a "thumbnail" size image that is stored in RAM memory 326 and supplied to the color LCD image display 332, which displays the captured image for the user to review. This low-resolution "thumbnail" size image, can be created as described in commonly-assigned U.S. Pat. No. 5,164,831 to Kuchta, et. al., the disclosure of which is herein incorporated by reference. The thumbnail image has 160×120 pixels, and is stored within the Exif version 2.1 image file along with the compressed full resolution image.

The electronic camera 6 is controlled by user controls 303, such as a series of user buttons including a shutter release (e.g., capture button) (not shown) which initiates a picture taking operation. The graphical user interface displayed on the color LCD image display 332 is controlled by the user interface portion of the firmware stored in the firmware memory 328.

After a series of images have been taken and stored on the removable memory card 330, the removable memory card 330 can be inserted into the card reader (not shown) in home computer 10. Alternatively, an interface cable 342 from can be used to connect between the host interface 322 in the electronic camera 6 and the CPU motherboard 12 in home computer system 10. The interface cable 342 can conform to, for example, the well known universal serial bus (USB) interface specification.

The digital camera 6 can create an image utilization file listing the images to be printed, as described in commonly assigned U.S. patent application Ser. No. 08/977,382, filed Nov. 24, 1997 to Parulski et al., the disclosure of which is herein incorporated by reference. This image utilization file can be a digital print order format (DPOF) file. The DPOF file can be used to automatically identify the digital images to be uploaded, replacing block 105 in FIG. 2.

The digital camera 6 can also store a service account identifier in the firmware memory 328, as described in commonly assigned U.S. patent application Ser. No. 09/534,469, filed Mar. 24, 2000 to Parulski, the disclosure of which is herein incorporated by reference. The service identification number can then be stored onto the removable flash memory 330, either as part of each image file, or as a separate digital record, so that it can be used to automatically access the service account for the user.

In another embodiment, the user uploads digital files containing motion videos, audio recordings, or scanned documents such as children's drawings, deeds, wills, etc. The service provider stores each uploaded file along with a designated date. At a later date, the user can select one or more of these uploaded files, from a list of file designators, such as file names, thumbnails depicting one or more images of a video clip, or an audio snippet providing a short audio recording. The user can then order services using the selected files, such as ordering a DVD disc containing one or more motion video files, a CD-R disc containing audio files, a hard copy print of a document, or an electronic copy of the motion video, audio recording, or scanned document file. The service provider uses a payment schedule that depends on the designated date associated with the selected file, bills the user according to the payment schedule, and provides the service requested by the user.

In another embodiment, the user selects, when uploading images, either "free storage" or "pay a monthly fee for storage" for the uploaded images. A designator indicating the user selection is stored in the Image List of the Service Account Information for each uploaded image. When "free storage" is selected, the payment schedule for ordered services using the uploaded images is the same as described in relation to block 122 of FIG. 2. When "pay a monthly fee for storage" is selected, a fixed payment schedule is used for ordered services, such as the "base price" column in FIG. 8B, regardless of the designated date the image was uploaded. In this case, the user is also billed monthly for storing the user's images. This embodiment enables the user to reduce the cost of photo products produced using a few particularly memorable images they have uploaded.

A computer program product can include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for practicing a method according to the present invention.

The invention has been described in detail with particular reference to certain preferred embodiments thereof, but it will be understood that variations and modifications can be effected within the spirit and scope of the invention.

PARTS LIST

2 CD reader
4 color scanner
6 digital camera
10 home computer system
12 CPU motherboard
14 display monitor
16 keyboard
18 mouse
20 hard drive
22 modem
30 Internet service provider
32 modem
34 computers/routers
36 channel
40 fulfillment center
42 network server
44 electronic database
46 billing system
48 bill issuing
50 product configuration system
52 album production controller
54 color hardcopy printers
56 album pages
58 hardcopy prints
60 album label printer
62 custom album cover
64 shipping container
66 photo product
68 frames
70 shipping label printer
74 shipping label
76 CD writer
78 PictureCD
100 block 102 block
104 block
105 block
107 block
109 block
111 block
113 block
118 block
119 block
120 block
122 block
123 block
124 block
126 block
128 block
150 print sizes
152 print size
154 print size
156 print size
158 print size
160 matte styles
162 solid mattes
164 textured mattes
166 background image mattes
170 picture frame styles
172 modem picture frame style
174 classic picture frame style
176 antique picture frame style
202 album size
204 album size
206 album size
208 radio buttons
210 background style
212 solid background style
214 textured backgrounds
216 background images
220 radio button
230 album types
232 bound albums
234 3-ring albums
236 20-ring albums
302 flash
303 users controls
304 control processor and timing generator circuit
306 clock drivers
308 autofocus and autoexposure detectors
310 zoom and focus motor drives
312 zoom lens
314 image sensor
316 analog signal processing and analog-to-digital converter circuit
318 DRAM buffer memory
320 processor
322 host interface
324 memory card interface
326 RAM memory
328 firmware memory
330 removable memory card
332 color LCD image display
342 interface cable
400 display screen
402 thumbnail images
402a thumbnail image
402b thumbnail image
402c thumbnail image
402d thumbnail image
404 arrow controls
406 upload indicator
408 number of images
410 total file size
412 transfer time
430 done icon
432 select all icon

What is claimed is:

1. A method of selecting images from a plurality of images previously transferred from a user and stored by a service provider, and ordering services to be provided utilizing the images, comprising:

a) establishing an account for the user with the service provider to permit the user to have access to ordered services;

b) receiving a plurality of images from the user and storing the plurality of images in an electronic database provided by the service provider;

displaying image designators for at least a subset of the images for viewing by the user;

d) the user selecting a service to be provided using at least one selected image from the plurality of images stored in the electronic database;

e) providing a price and a lower discounted price for the selected service; and f) using the discounted price if the user deletes at least one of the plurality of images from the electronic database;

wherein the price is provided using a payment schedual that depends upon a designated that depends upon a designated date associated with the selected image;

wherein the payment schedual provides different service charges for the same service when such service is ordered at different periods of time measured from the designated date;

wherein the services which can be selected includes providing hard copy prints, transferring images to another memory location, or producing an album.

2. The method of claim 1 wherein the user account includes a payment identifier which is used to bill the user.

3. The method of claim 1 wherein the selected service is producing hard copy prints of the at least one image.

4. The method of claim 3 wherein the hard copy prints are sent by the U.S. postal service or a private carrier to the user's designee.

5. The method of claim 3 wherein the hard copy prints are sent to a user designee address provided in the user account.

6. The method of claim 3 wherein the hard copy prints are delivered to a retail location.

7. A method of ordering services to be provided utilizing images from a plurality of images previously stored in an electronic database, and comprising:

a) recieving a plurality of images and storing the plurality of images in the electronic database;

b) enabling a user to select a service to be provided using at least one image from the plurality of images stored in the electronic database, c) providing a price for the selected service;

d) discounting the price in response to an action of the user to delete at least one of the plurality of images from th electronic database; and e) providing the selected service and billing the user the discounted price.

8. The method of claim 7 wherein the services which can be selected includes providing hard copy prints, transferring images to another memory location, or producing and album.

9. The method of claim 7 wherein the user account uncludes a payment identifier which is used to bill the user.

10. The method of claim 7 wherein the selected service is producing hard copy prints of the at least one image.

11. The method of claim 10 wherein the hard copy prints are sent by the U.S. postal service or a private carrier to the user's designee.

12. The method of claim 10 wherein the hard copy prints are sent to a user designee address provided in the user account.

13. The method of claim 10 wherein the hard copy prints are delivered to a retail location.

* * * * *

UNITED STATES PATENT AND TRADEMARK OFFICE
CERTIFICATE OF CORRECTION

PATENT NO. : 7,136,837 B2 Page 1 of 1
APPLICATION NO. : 10/842201
DATED : November 14, 2006
INVENTOR(S) : William M. Jackson et al.

It is certified that error appears in the above-identified patent and that said Letters Patent is hereby corrected as shown below:

Title Page, under "Notice:"  Insert --This patent is subject to a terminal disclaimer.--.
Column 16, line 18          Insert --c)--.
Column 16, line 28          Delete "schedual" and insert --schedule--.
Column 16, line 31          Delete "schedual" and insert --schedule--.
Column 16, line 61          after the word "from" delete "th" and insert --the--.

Signed and Sealed this

Twentieth Day of March, 2007

JON W. DUDAS
*Director of the United States Patent and Trademark Office*